(12) United States Patent
Samuels

(10) Patent No.: US 7,216,376 B2
(45) Date of Patent: May 15, 2007

(54) HYGIENE STATION FOR INDIVIDUALS

(75) Inventor: Allen Samuels, Ann Arbor, MI (US)

(73) Assignee: Regents at The University of Michigan, Ann Arbor, MI (US)

( * ) Notice: Subject to any disclaimer, the term of this patent is extended or adjusted under 35 U.S.C. 154(b) by 214 days.

(21) Appl. No.: 10/804,445

(22) Filed: Mar. 19, 2004

(65) Prior Publication Data

US 2004/0210997 A1    Oct. 28, 2004

Related U.S. Application Data

(60) Provisional application No. 60/456,292, filed on Mar. 20, 2003.

(51) Int. Cl.
*A47K 13/14* (2006.01)
(52) U.S. Cl. ............................... 4/484; 4/239
(58) Field of Classification Search .................. 4/239, 4/315, 484, DIG. 5
See application file for complete search history.

(56) References Cited

U.S. PATENT DOCUMENTS

| 41,602 A | 2/1864 | Campbell .................... 312/201 |
| 49,766 A | 9/1865 | Koch .............................. 4/664 |
| 68,802 A | 9/1867 | Staples ........................ 312/210 |
| 275,837 A | 4/1883 | McLaughlin ....................... 5/1 |
| 391,599 A | 10/1888 | Elwell ........................... 4/665 |
| 1,077,199 A | 10/1913 | James ............................ 4/547 |
| 1,379,318 A | 5/1921 | Steinkamp ..................... 4/664 |
| 1,525,605 A | 2/1925 | Dry ................................ 5/604 |
| 1,527,340 A * | 2/1925 | Wood ............................. 4/484 |
| 1,730,547 A | 10/1929 | Wallace ......................... 4/664 |
| 1,756,635 A | 4/1930 | Dennis et al. ................. 4/664 |
| 1,763,209 A | 6/1930 | Ayers et al. .................... 4/663 |
| 1,859,859 A | 5/1932 | Zook ............................. 4/596 |
| 1,978,871 A * | 10/1934 | Thuren ......................... 4/484 |
| 2,173,185 A | 9/1939 | Stanton ......................... 4/663 |
| 2,198,605 A | 4/1940 | Faber ............................ 4/663 |

(Continued)

FOREIGN PATENT DOCUMENTS

DE          9001456          6/1991

(Continued)

OTHER PUBLICATIONS

International Search Report for Appln. No. PCT/US2004/008562 dated Nov. 8, 2004, 16 pgs.

*Primary Examiner*—Robert M. Fetsuga
(74) *Attorney, Agent, or Firm*—Dobrusin & Thennisch PC

(57) ABSTRACT

The present invention comprises a disposable hygiene device with a toilet seat with a top and bottom surfaces, where the toilet seat folds for storage before or after use. A receptacle is attached to the bottom surface of the toilet seat. After use, an adhesive on the top surface of the toilet seat is exposed by the removal of a protective layer. The toilet seat may then be folded onto itself to seal the hygiene device for easy disposal. The toilet seat may also include handles or an extension to ease proper orientation and use of the disposable hygiene device. The present invention also includes hygiene stations, preferably portable, that may be used with the disposable hygiene device, hygiene stations that include rotatable, extendable and height adjustable bathroom fixtures, and hygiene stations have a common connection point for inputs and outputs.

5 Claims, 4 Drawing Sheets

U.S. PATENT DOCUMENTS

| | | | |
|---|---|---|---|
| 2,355,615 A | 8/1944 | Helmuth | 4/553 |
| 2,438,665 A | 3/1948 | Hesse | 4/553 |
| 2,500,739 A | 3/1950 | Beem | 5/605 |
| 2,500,740 A | 3/1950 | Beem | 5/606 |
| 2,500,743 A | 3/1950 | Beem et al. | 5/604 |
| 3,381,315 A * | 5/1968 | Glassberg | 4/484 |
| 3,458,871 A | 8/1969 | Rivetti Di Valcervo | 4/664 |
| 3,590,392 A | 7/1971 | Hollander et al. | 4/663 |
| 3,808,607 A | 5/1974 | Harder | 4/545 |
| 3,943,583 A | 3/1976 | Ishikawa | 5/605 |
| 3,952,336 A * | 4/1976 | Kunter et al. | 4/484 X |
| 4,718,131 A | 1/1988 | Kitamura et al. | 4/663 |
| 4,780,919 A | 11/1988 | Harrison | 5/600 |
| 4,996,727 A | 3/1991 | Wyatt | 4/484 |
| 5,060,325 A | 10/1991 | Carnahan et al. | 5/605 |
| 5,285,540 A | 2/1994 | Putz | 4/661 |
| 5,384,920 A | 1/1995 | Havens | 4/480 |
| 5,647,074 A | 7/1997 | White, Jr. et al. | 4/664 |
| 6,109,189 A | 8/2000 | Tarver | 108/48 |
| 6,151,738 A | 11/2000 | Arr | 5/661 |
| 6,532,605 B1 * | 3/2003 | Howell | 4/484 |

FOREIGN PATENT DOCUMENTS

| | | |
|---|---|---|
| DE | 4013210 | 10/1991 |
| DE | 29815217 | 9/1999 |
| GB | 2376183 | 12/2002 |

* cited by examiner

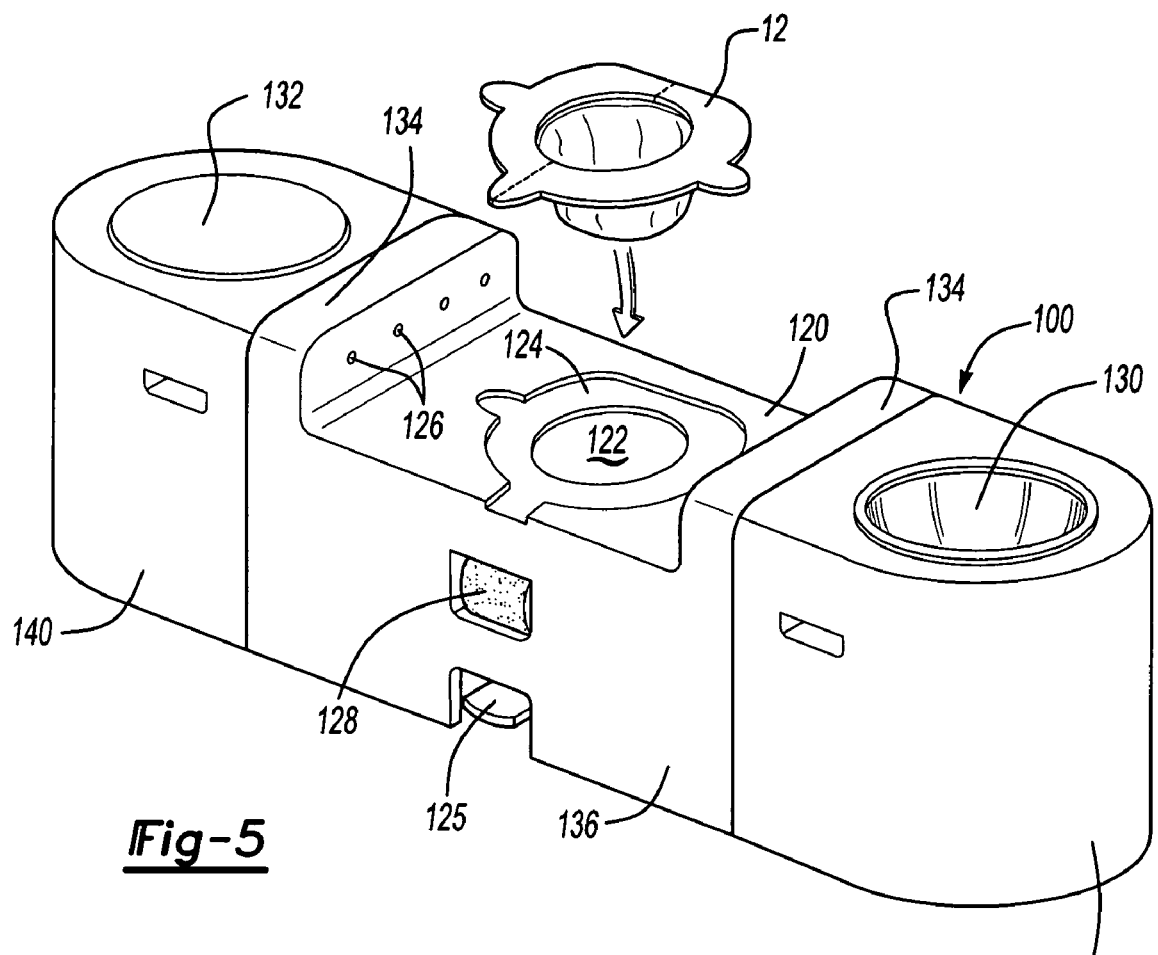
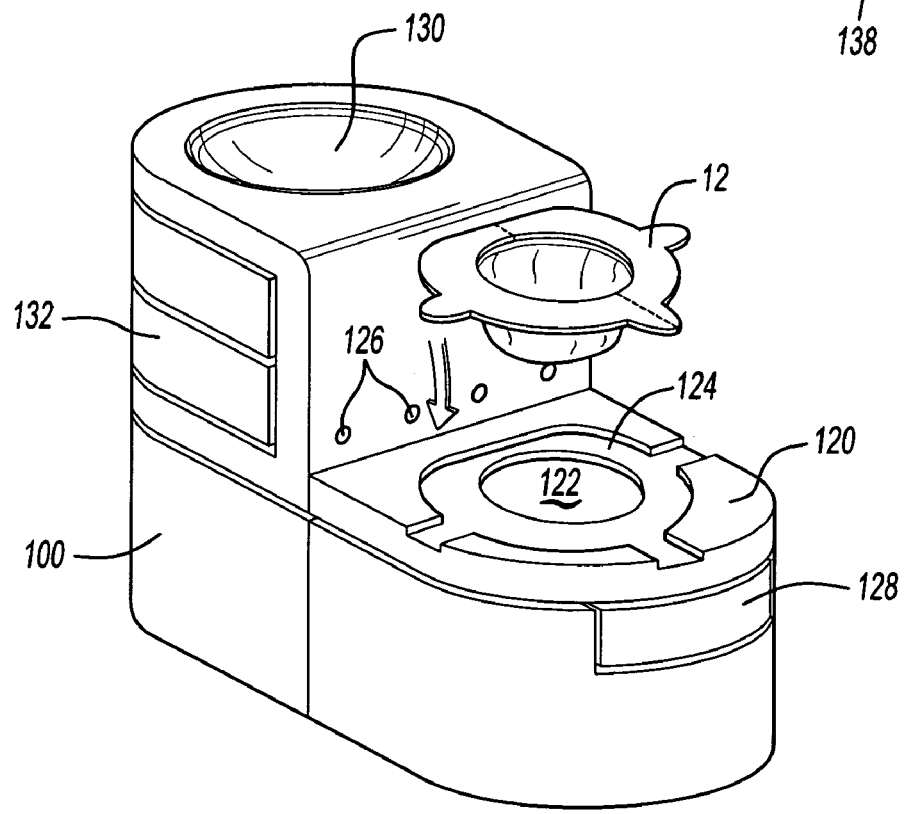

HYGIENE STATION FOR INDIVIDUALS

CLAIM OF PRIORITY

This application claims the benefit of U.S. Provisional application 60/456,292 filed on Mar. 20, 2003.

FIELD OF INVENTION

The present invention relates generally to hygiene devices and hygiene stations. More particularly, the present invention relates to disposable hygiene devices, mobile hygiene stations and integrated hygiene stations. The present inventions are advantageously used by individuals having mental or physical impairments that make completion of hygiene tasks difficult or impossible. The present inventions are also advantageously used by individuals in locations where completion of hygiene tasks is difficult.

BACKGROUND OF THE INVENTION

Typically, individuals have been restricted to conventional bathrooms in performing hygiene functions, such as using the toilet, washing and or grooming, regardless of their age, physical abilities or mental faculties. However, conventional bathrooms can be problematic for various individuals, such as persons having physical or cognitive disabilities. This is specifically the case for individuals that use mobility assisting devices such as wheelchairs, canes, walkers or the like. As an example, conventional bathroom designs, in both home and institutional environments, may require that an individual in a wheelchair perform a complex 'dance' to perform hygiene tasks including traversing around objects and through doors to get to the bathroom, manipulate the door, transfer themselves from the wheel to the toilet, then again from the toilet to the wheelchair to wash his or her hands, and then reverse their traverse. On top of this, conventional bathroom designs also tend to offer insufficient space to allow a caregiver to assist the individual.

In addition, there are various times and situations where performing hygiene functions is inconvenient or unsanitary. For example, truckers, RV-ers, campers and other travelers may not have ready access to bathrooms. In addition, bathrooms that are available may not be suitable as they are not suitably clean.

As such, there is a need for disposable hygiene devices, portable hygiene stations and integrated hygiene stations that provides greater accessibility to individuals in all places including bathrooms. More particularly, there is a need for hygiene devices and hygiene stations designed to assist individuals and caregivers in the performance of toilet and hygiene tasks.

SUMMARY OF THE INVENTION

The present invention comprises a disposable hygiene device with a toilet seat with a top and bottom surfaces, where the toilet seat folds for storage before or after use. A receptacle is attached to the bottom surface of the toilet seat. After use, an adhesive on the top surface of the toilet seat is exposed by the removal of a protective layer. The toilet seat may then be folded onto itself to seal the hygiene device for easy disposal. The toilet seat may also include handles or an extension to ease proper orientation and use of the disposable hygiene device. The present invention also includes hygiene stations, preferably portable, that may be used with the disposable hygiene device, hygiene stations that include rotatable, extendable and height adjustable bathroom fixtures, and hygiene stations have a common connection point for inputs and outputs.

DESCRIPTION OF THE DRAWINGS

FIG. 5 illustrates another perspective view the second preferred embodiment of the hygiene station along with other modules.

FIG. 6 illustrates a perspective view of a third preferred embodiment of a hygiene station for use in combination with the disposable hygiene device.

DESCRIPTION OF THE INVENTION

Figure 1:
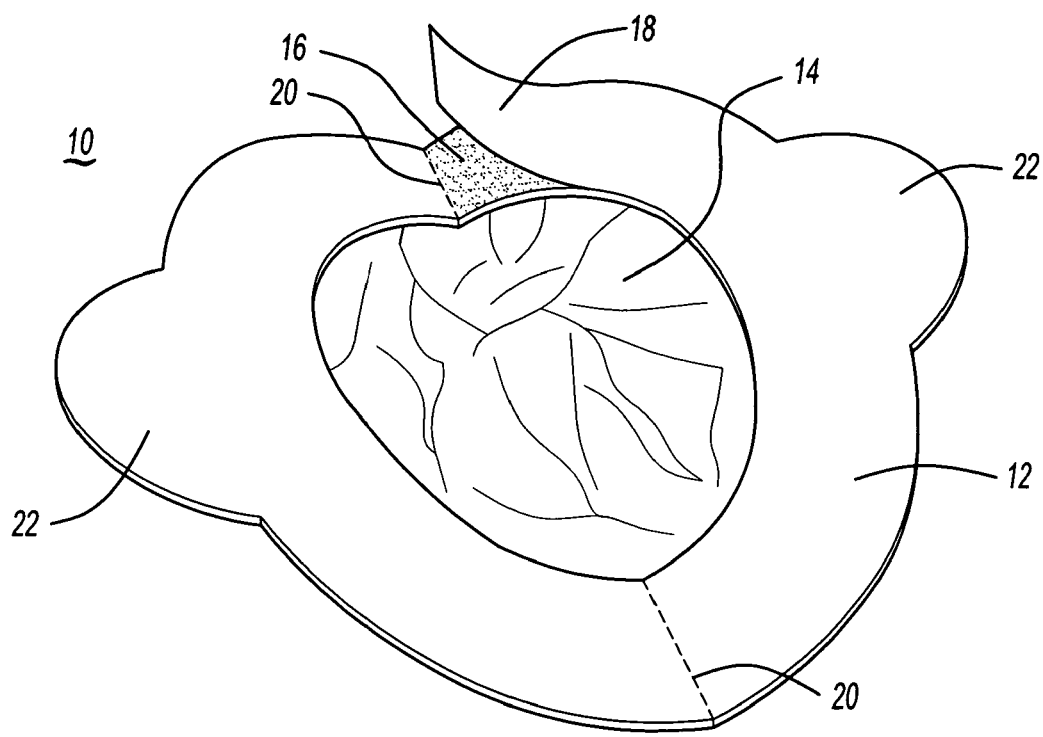
FIG. 1 illustrates a perspective view a disposable hygiene device according to the present invention.
Figure 2:
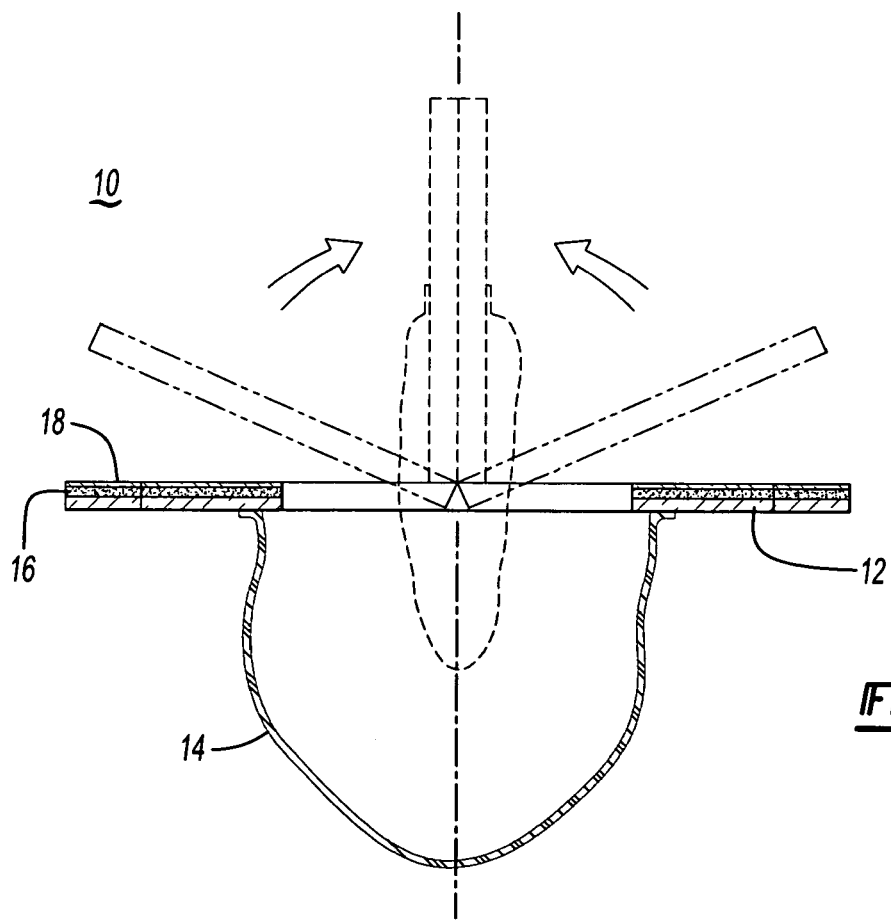
FIG. 2 illustrates a cross sectional view a disposable hygiene device according to the present invention.

The present invention, referring to FIGS. 1 and 2, is a disposable hygiene device 10 that includes a toilet seat 12 that is generally doughnut shaped with a hole through the middle. Attached to the underside of the toilet seat 12 is a receptacle 14. Together, the toilet seat and the receptacle may be utilized for the toileting functions of an individual.

For those who are able, the disposable hygiene device may be held in place during use. Alternately, as described below, the disposable hygiene device may be supported by a hygiene station during use. In either situation, the disposable hygiene device provides a convenient method of accomplishing the toileting function when a toilet is not available or accessible. Also, even when a toilet is available and accessible, the disposable hygiene device provides a sanitary method of accomplishing the toileting function or a convenient method of collecting samples to be used in a variety of medical tests.

In one preferred embodiment, the topside of the toilet seat 12 includes an adhesive 16 covered by a protective layer 18 that is peel removable. After use, the protective layer may be removed to expose the adhesive. After exposure, the adhesive may be adhered to a separate cover panel or layer (not shown) to seal the receptacle. In a preferred embodiment, one portion of the toilet seat is adhered to another portion of the toilet seat to form a sealed receptacle. To facilitate the adhering the toilet seat to itself, the toilet seat may include one or more fold lines 20. The fold lines ease the requirements for folding the toilet seat on to itself. Preferably, the toilet seat is folded in half.

The toilet seat may include a pair of handles 22 located opposite each other. The handles facilitate holding the device in place during use. For example, the individual may use the handles to hold the device during use. The handles also provide a visual orientation cue for the proper use of the device, which may be important for individuals with cognitive difficulties.

Figure 3:
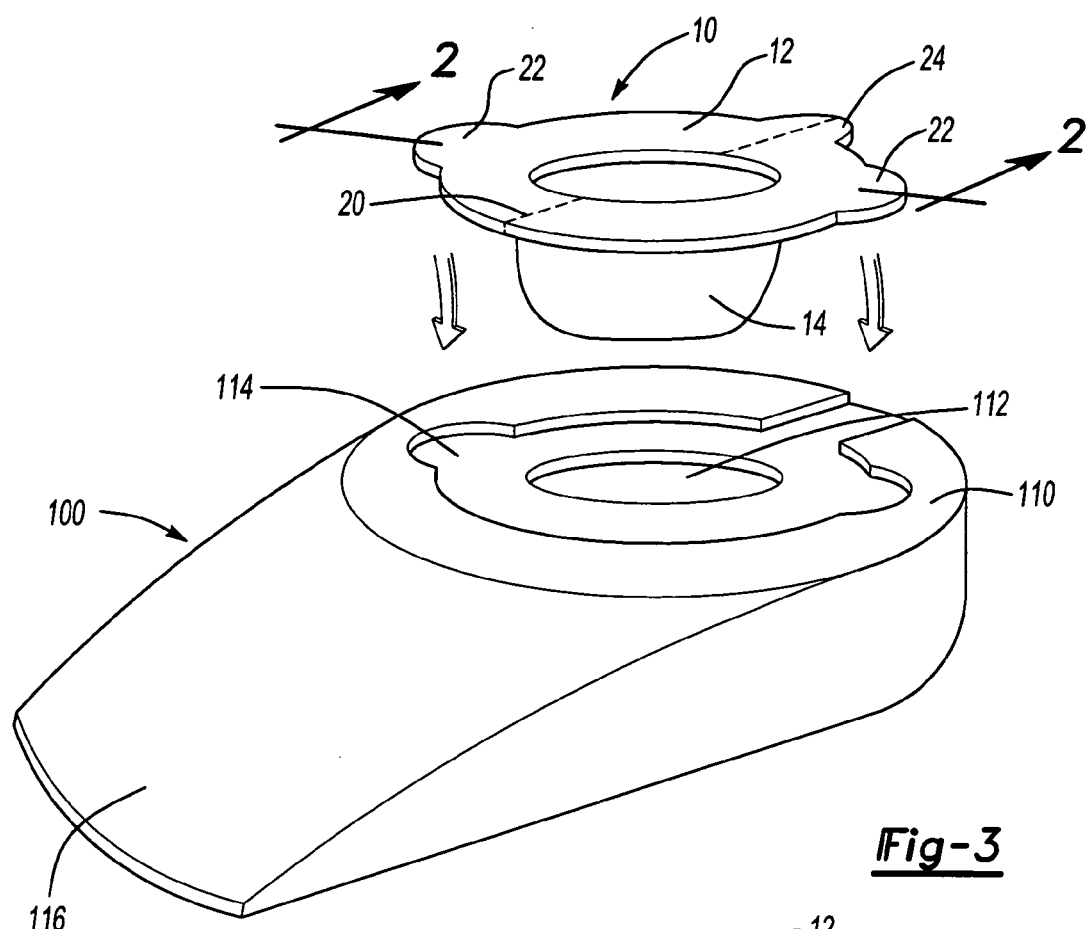
FIG. 3 illustrates a perspective view of a first preferred embodiment of a hygiene station for use in combination with the disposable hygiene device.

The toilet seat may also contain other visual orientation cues in the form of an extension 24 as best seen in FIG. 3. Any extension will be similar to a handle, except that it will be without a mate. Typically, the extension will be placed toward the front of the device. The extension may also serve other functions such as a urine guard to help direct urine to the receptacle. Additional visual orientation cues may be used, such as markings on the toilet seat or receptacle to indicate front, back, top or bottom and/or proper or improper use of the device.

As discussed below, the handles and/or extension may also help orient the device on a hygiene station.

The toilet seat may be made of any material, whether considered disposable or not. For example, metal, plastic, ceramic, cardboard, paper or the like are all suitable materials for the toilet seat. The preferred embodiment includes a toilet seat made of a material that is cost effective to be disposed after a single use (i.e. disposable) and biodegradable. Cardboard and paper are preferred materials for several additional reasons. These materials can readily be made sturdy enough to remain substantially flat surface during use while also being weak enough to permit folding after use. Furthermore, cardboard and paper are readily made to the desired shape, such as by die cutting. These materials may also readily have fold lines created through a number of techniques including die cutting, clamping or perforation. In addition, these materials readily accept adhesive and adhere with cost effective adhesives. In one preferred embodiment, the cardboard or paper toilet seat is coated with or impregnated with a water proof or water resistant material to help prevent decomposition of the toilet seat in the presence of water.

The receptacle may be attached to the toilet seat in any manner that generally insures a water tight seal between the receptacle and the toilet seat; e.g. an adhesive. The receptacle may also be heat staked or otherwise melted to attach it to the toilet seat. This may be particularly preferred when the toilet seat contains plastic or a plastic cover layer.

The receptacle may be made of any material that is capable of containing the results of the toileting functions. A relatively flexible, water proof plastic bag is preferred. In a more preferred embodiment, a clear plastic bag is utilized to facilitate visual inspection of the resultant waste by a caregiver. A variety of indicators may be utilized on the receptacle to notify when a receptacle has been used e.g. a wetness indicator.

The adhesive on the topside of the toilet seat may be spread across substantially all the area of the toilet seat or spread across only a portion of the toilet seat. Preferably, at a minimum, adhesive is applied on the toilet seat around at least half the circumference of the toilet seat. Thus, when folded, a proper seal can be insured. In a preferred embodiment, the adhesive is spread around the whole circumference of the toilet seat. The adhesive may be applied in any manner or pattern that minimizes material costs while leading to a sealed disposable hygiene device after use.

The protective layer is typically sized and shaped to conform to the size and shape of the toilet seat. However, to save materials, the protective layer may be sized and shaped to cover only those areas of the toilet seat which contain the adhesive. Furthermore, the protective layer may also include a tab, loop or other device which facilitates peeling the protective layer away from the adhesive. Such a feature may be particularly advantageous for individuals who have limited physical or cognitive abilities. The protective layer may be any suitable material that keeps the adhesive from sticking to the individual during use and preferably is a wax or plastic coated paper. While a single piece protective layer is preferred a protective layer with multiple pieces may be suitable.

Manufacture of the hygiene device may be accomplished using methods well known with the art. In one preferred embodiment, manufacturing includes layering a sheet of toilet seat material with a protective layer, where the toilet sheet material and the protective layer are at least partially separated from each other by an adhesive. Cutting the toilet seat to shape may be accomplished by die cutting or other suitable technique. Attaching the receptacle to the toilet may be accomplished with any suitable technique. There is no particular order in which the manufacturing steps need to be carried out, although layering followed by cutting followed by attaching is the preferred order.

The device may include one or more facilitating components that facilitate the toileting functions or disposable of the used device. For example, odor control may encourage an individual to use this type of hygiene device or station again. Odor control mechanism may be a part of the device such as scented material within the receptacle, as part of the receptacle material, as part of the toilet seat or as part of the peel exposed adhesive. In one embodiment, the act of removing the protective layer causes the release of covering scent. Other facilitating components include a portion of toilet tissue, sanitary wipes or gel to provide hand cleaning after use, and/or instructions on the proper use and disposal of the device. In one preferred embodiment, both toilet paper and sanitary wipes are held in a dispenser at or near the front of the toilet seat or on the extension, if present. Another facilitating device may include a hydroscopic material contained with the receptacle. Such a material may facilitate the disposal of the device.

The device may be packaged in an envelope or bag that holds the device and some or all of the facilitating components as well. The envelope may serve as an addition disposal bag into which the used device may be place along with the other used components. Such a double layer waste disposal system may be required by some municipalities for the disposal of human waste. The envelope may also be resealable. The use of an envelope also would permit the hygiene device to be easily sold in a piece by piece manner, such as in public bathrooms.

The present invention also includes a hygiene station that may be used separately or in combination with the hygiene device described above. Regardless, the hygiene stations of the present invention permit an individual to accomplish toileting functions with a good deal of dignity even if the individual is of limited mobility.

In a first embodiment, the hygiene station is intended for use by individuals that are bed bound; where the toilet is brought to the bed; the essence of a portable hygiene station. By themselves or with the help of a caregiver, an individual may place a hygiene station with a hygiene device in the bed to permit the accomplishment of toileting functions without the need to leave the bed. Referring to FIG. 3, the hygiene station 100 includes a main portion 110 that includes a well 112. The receptacle 14 of the hygiene device 10 is received in the well when the hygiene device is placed on the hygiene station (assembly is generally shown by the arrows). The main portion may also include a recessed portion 114 that is adapted to receive, and otherwise support, the toilet seat 12 of the hygiene device 10. Preferably, the toilet seat 12 is seated within the recessed portion 114 when assembled so that a relatively flat top surface on the main portion 110 is presented to the individual. In a preferred embodiment, the recessed portion is shaped to also receive the handles and the extension that may be part of the toilet seat. In this way, both the hygiene device and the hygiene station provide visual cues on how properly assemble the hygiene device to the hygiene station.

In addition to the main portion 110, the hygiene station 100 also includes a wedge 116. The wedge provides a sloped incline generally from the bottom surface of the main portion to the top surface. With the incline, an individual may find it easier to maneuver into proper position to use the hygiene device. The wedge means that an individual with a minimum of upper body strength could slide themselves up the incline and into position or vice versa. In the absence of the wedge, an individual would have to lift themselves up while simultaneously sliding the hygiene device into or out of place. The wedge also means that an individual caregiver could also maneuver a user into proper position with a minimum of help from the user or from another caregiver, by either moving the individual or the device into or out of place.

The hygiene device may be made of any material sturdy enough to support the weight of the individual, such as metal or plastic. Preferably, a clear plastic is utilized to facilitate a visual inspection of the receptacle by a caregiver. The hygiene device also preferably is made of a material that resists sliding on bed linens. In the alternative, the hygiene device may include a layer or coating on its bottom surface that helps resist sliding on bed linens.

In a second embodiment, the hygiene station is intended for use by individuals that have limited walking capabilities or have limited access to traditional toilet facilities (e.g. truckers, RV-ers, campers and the like).

Referring to FIGS. 4–7, several different embodiments of the hygiene station are depicted. The depicted hygiene stations 100 have in common that they have a support for an individual in a sitting position; that is, they have a seat (e.g. a chair or a bench) with a support ring or surface 120 (shown in phantom on FIG. 7) to hold the toilet seat 12 of the hygiene device and an open space or well 122 in which to receive the receptacle of the hygiene device (assembly is generally shown by the one or more arrows).

Figure 4:
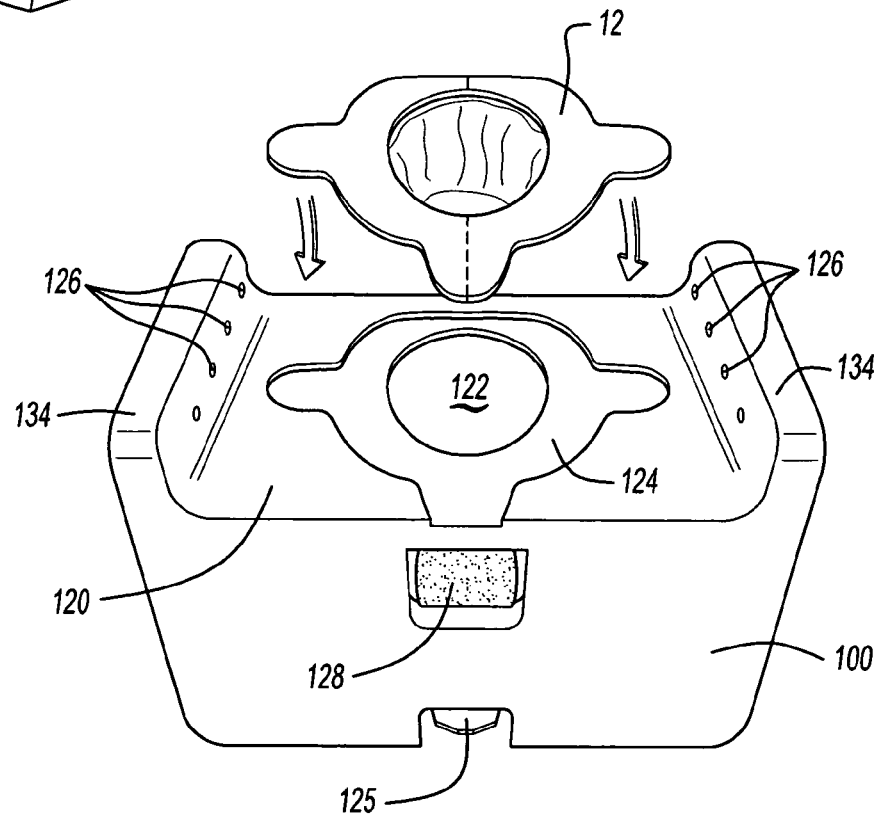
FIG. 4 illustrates a perspective view of a second preferred embodiment of a hygiene station for use in combination with the disposable hygiene device.
Figure 7:
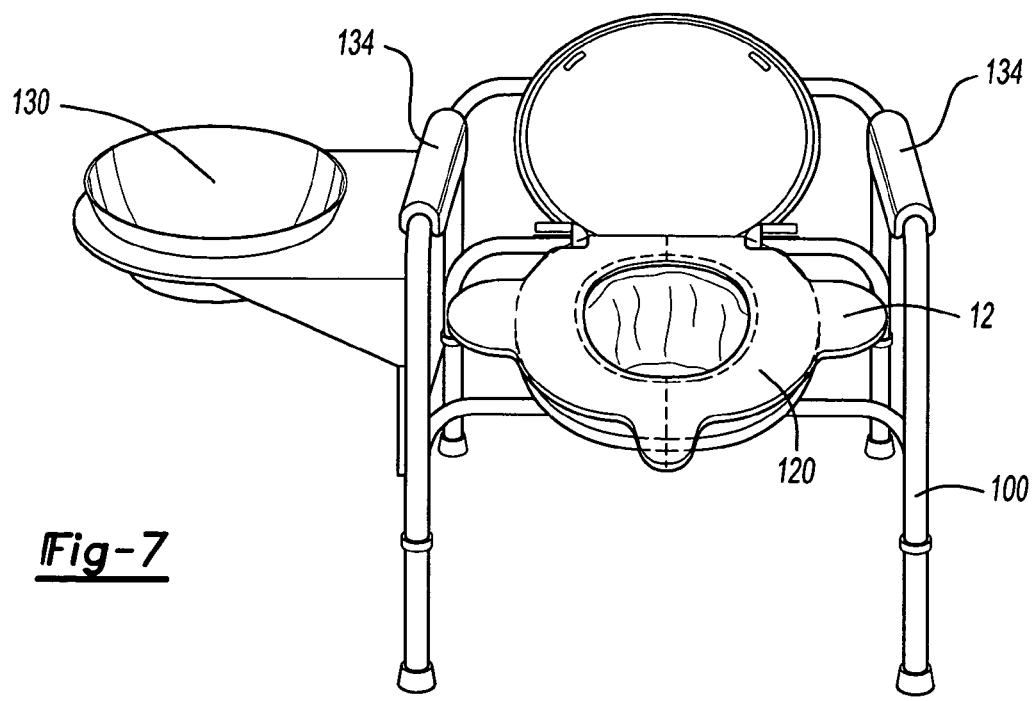
FIG. 7 illustrates a perspective view of a fourth preferred embodiment of a hygiene station for use in combination with the disposable hygiene device.

The hygiene stations shown in FIG. 4–6 each include a support ring or surface 120 with a recessed portion 124 around the well 122 that is adapted to receive the toilet seat of the hygiene device, as discussed above with respect to the first embodiment of hygiene station. However, such a recessed portion is not necessary, as shown in FIG. 7, where the hygiene device is merely placed on an un-recessed surface 120.

The hygiene stations are sized and constructed to permit easy movement of the station to and from the location where the toileting function will be carried out, whether that is bedside, within a vehicle or elsewhere. For example, the hygiene stations shown in FIGS. 4–6 may include wheels or sliders to permit the station to be moved to bedside. The station shown in FIG. 7 would sufficiently light weight so that an individual or caregiver could move the station by lifting. In another embodiment not shown in the figures, the hygiene station may also attach to or hang on a door.

Although the hygiene stations shown in FIGS. 4–7 are preferably portable, they may be temporarily or permanently affixed to a floor, a wall, a door or the like of a building or vehicle to prevent the hygiene station from moving. Alternately, as seen on FIGS. 4 and 5, a wheel lock 125 may be used to temporarily prevent the hygiene station from moving or being moved.

In addition to the toilet, the hygiene stations may include a variety of facilitating components that facilitate the toileting functions or disposable of the used device. These facilitating components may be instead of or in addition to any such components that may be part of the hygiene device. For example, as seen in FIGS. 4–6, an odor control mechanism may provide fresh air or odor removal through a plurality of vents 126. These vents may also provide temperature conditioned air. Lights on the hygiene station may be utilized to provide visual cues as to the proper use of the stations or generally to illuminate the position of the station. As needed, the hygiene station may contain a power source (e.g. battery) or a power cord to connect to the building or vehicle power supply.

As seen in FIGS. 4–6, the hygiene station may include a source of toilet paper 128. A basin 130 for washing may also be included, as seen in FIGS. 5–7, in the hygiene stations. The basins may be removable or permanent to the hygiene station. Alternately, a source of sanitary wipes or gel may be provided. Storage compartments 132 (including sealable compartments) may also be included in the hygiene stations, as seen in FIGS. 5 and 6.

As seen in FIGS. 4, 5 and 7, the hygiene stations preferably include arms or support grips 134 on either side of the open space or well, although as seen in FIG. 6, this is not necessarily the case. Indeed, the absence of arms may be advantageous, as the embodiment of FIG. 6 permits an individual to face the basin while performing toileting functions, so that the individual does not need to reposition themselves in order wash their hands.

Some of the facilitating components of the hygiene stations discussed above may be modular in they can be added, removed or used independently of each other, as necessity dictates. For example, as seen in FIG. 5, the hygiene station 100 includes a main toilet module 136, a basin module 138 and a storage module 140 as an integrated, portable unit. The main toilet module is shown on its own in FIG. 4. Handles, grips or other devices may be used to facilitate adding, removing or otherwise moving the modules.

The hygiene stations are preferably used with the hygiene device; however, this is not necessarily the case. The depicted hygiene stations may include electrical and plumbing connections to the building or vehicle in which they reside. Alternately, the hygiene stations may have a self-contained source of water, a waste reservoir and/or an electrical source (e.g. a battery).

Figure 8:
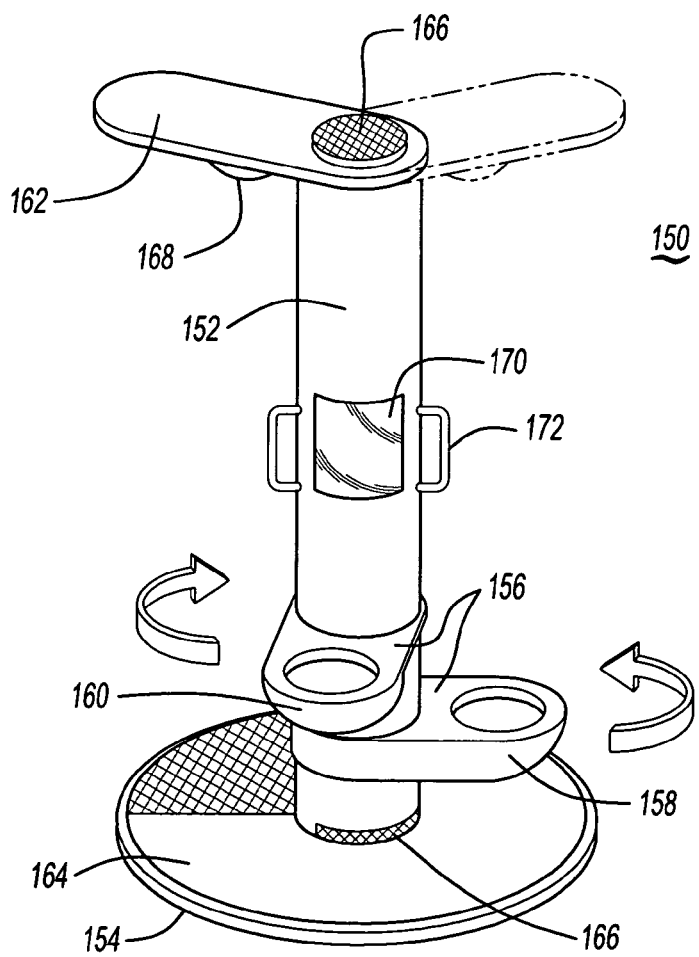
FIG. 8 illustrates a perspective view of another hygiene station according to the present invention.

In another aspect, the present invention comprises a multi-functional hygiene station where several functions are integrated into a single unit. Referring to FIG. 8, the hygiene station 150 includes central column 152 connected to a base 154. To central column, a number of bathroom fixtures 156 such as a toilet 158, a sink 160 and a bathing unit 162 are attached. In this particular embodiment, the bathing unit is a shower, however, a bathtub bathing unit is also contemplated.

The bathroom fixtures are preferably capable of at least one of the following actions to ease an individual's use of the bathroom fixtures: rotating about the central column (shown by arrows and phantom views in FIG. 8); adjusting height from the floor, and/or extending from the central column. The range of motion for each bathroom fixture is preferably significant; however, even movement of a few inches might sufficient. While bathroom fixtures preferably are able to make a 360° rotation, such freedom of movement is not required.

The permitted movement of the bathroom fixtures eases the strain of accomplishing multiple hygiene functions at one time. For example, once seated on the toilet, the individual may rotate the sink to bring it within reach so that the individual does not need to move from the toilet to wash. In another situation, an individual can shower while seating on the toilet by rotating the shower. Height adjustable bathroom fixtures are advantageous to ease an individual's use of the fixture. For example, the sink may rise up so that an individual in a wheel can roll underneath the sink. A sink that extends from the central column would offer similar benefits to an individual in a wheel chair or an individual with a walker.

In a preferred embodiment, the sink is located above the toilet on the central column and both are rotatable and height adjustable, while the shower is rotatable. In another embodiment, the bathroom fixtures are integrated into a single platform connected to the central column where the platform is rotatable and height adjustable. In this embodiment, the central column may be located through the substantial center of the platform or may be located to provide a cantilevered platform. In another preferred embodiment, the toilet and sink are located back-to-back (as seen in FIG. 6), and the shower functionality is provided by a wand stored on the side of the hygiene station. Stated alternately, the central column does not necessarily extend to a height or length that is greater than the sink, toilet or bathtub.

The central column of the hygiene station provides a unified connection point for the source and drain plumbing that may be used by the hygiene station. Instead of requiring hot and cold water lines for each of the toilet, sink and shower, a single set of hot and cold water lines can be provided through the central column. A similar advantage is realized with respect to the drains for the hygiene station. Such unified source and drain plumbing reduces the cost of installation and maintenance. In a preferred embodiment, all the bathroom fixture have common water source lines and at least the toilet and sink have common drain lines. Where a bathtub is included, it preferably shares a drain with the toilet and sink. In addition, a unified connection point permits a hygiene station to be modularly built in the factory or as part of the installation of the station. The unified connection point typically be at or near the floor or wall, however the connection point may be near the ceiling.

The hygiene station may also include a variety of other facilitating components that help with the toileting, washing and/or grooming functions. For example, the hygiene station may include lighting, storage, mirrors, support rails, a water collection system, a ventilation system, a heating and cooling system, a humidity control system, an audio-visual system, a monitoring system, and combinations thereof.

One example of a water collection system would be a floor pan that directs shower water to a drain with a sloped floor and/or with a barrier on the floor.

Besides entertainment, the audio-visual system may also provide task prompting to the user who may require such prompting to adequately complete toileting or other hygiene functions, such as washing, tooth brushing, etc. The audio-visual system may also provide warnings such as regarding water temperature or slick floors.

The monitoring system may include both video and audio monitoring capabilities, including items such as microphones and speakers to facilitate two-way communication between the individual using the hygiene station and a remotely located caregiver. The monitoring system may also include a call button that the individual could use to request assistance.

Doors and panels on the central column may be used to give or restrict access to the various mechanisms and components of the hygiene station. For example, a medicine cabinet door may provide an individual with access to storage, whereas a locked access panel may restrict the individual's access to the plumbing system.

In a preferred embodiment, the central column contains all of these facilitating components. As seen in FIG. 8, the hygiene station 150 includes a floor pan 164, a ventilation system 166, a light 168, a mirror 170 with storage behind it, and support rails 172.

In addition to the water source and drain, the hygiene station also preferably has an electrical power source, such as being tied into the power system of the building or vehicle where the hygiene station is located. Other inputs may also be necessary, such as wire or computer cables to provide information for the audio-visual system on the hygiene station.

The base to which the central column is attached is typically a floor or ceiling, thus providing a central column that is substantially vertical. In another embodiment, the central column is attached to a wall or other vertical structure, thus providing a central column that is substantially horizontal. In either case, the base may be portable or part of a permanent structure. In addition to the roughly cylindrical shape of the central column shown in the figures, other shapes are also possible including regular and irregular polygons. In one embodiment, the central column is a partition (e.g. a C-shaped partition) or stall that provides the individual with privacy during use of a station located in a public place.

It will be further appreciated that functions or structures of a plurality of components or steps may be combined into a single component or step, or the functions or structures of one step or component may be split among plural steps or components. The present invention contemplates all of these combinations. Unless stated otherwise, dimensions and geometries of the various structures depicted herein are not intended to be restrictive of the invention, and other dimensions or geometries are possible. Plural structural components or steps can be provided by a single integrated structure or step. Alternatively, a single integrated structure or step might be divided into separate plural components or steps.

In addition, while a feature of the present invention may have been described in the context of only one of the illustrated embodiments, such feature may be combined with one or more other features of other embodiments, for any given application. For example, one possible combination would be a hygiene station that resembles the station depicted in FIG. 8 that is not plumbed, but rather uses the described hygiene device in combination with a sink and/or shower that draws water from a self contained reservoir. It will also be appreciated from the above that the fabrication of the unique structures herein and the operation thereof also constitute methods in accordance with the present invention.

The explanations and illustrations presented herein are intended to acquaint others skilled in the art with the invention, its principles, and its practical application. Those skilled in the art may adapt and apply the invention in its numerous forms, as may be best suited to the requirements of a particular use. Accordingly, the specific embodiments of the present invention as set forth are not intended as being exhaustive or limiting of the invention. The scope of the invention should, therefore, be determined not with reference to the above description, but should instead be determined with reference to the appended claims, along with the full scope of equivalents to which such claims are entitled. The disclosures of all articles and references, including patent applications and publications, are incorporated by reference for all purposes.

I claim:

1. A disposable hygiene device, comprising:
   a substantially flat toilet seat with a top surface, a bottom surface and at least one pair of handles adapted to fold for storage before or after use;
   a receptacle attached to the bottom surface of the toilet seat; and
   an adhesive located on the top surface that is exposed after use by removal of a protective covering,
   wherein the toilet seat further comprises a visual orientation cue on the toilet seat that comprises an extension of the toilet seat extending from a front of the toilet seat.

2. The disposable hygiene device of claim 1, wherein the toilet seat comprises at least one fold-line that promotes folding of the toilet seat.

3. The disposable hygiene device of claim 1, further comprising a portable hygiene station comprising a support ring capable of receiving the toilet seat.

4. The disposable hygiene device of claim 3, wherein the supporting ring comprises a visual orientation cue to facilitate placement of the toilet seat on the supporting ring.

5. The disposable hygiene device of claim 1, wherein the portable hygiene station comprises a transparent material to facilitate identification of completion of a hygiene task.

* * * * *